(12) United States Patent
Doguchi et al.

(10) Patent No.: US 8,202,214 B2
(45) Date of Patent: Jun. 19, 2012

(54) ENDOSCOPE

(75) Inventors: Nobuyuki Doguchi, Hino (JP); Hironobu Ichimura, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 1222 days.

(21) Appl. No.: 11/917,436

(22) PCT Filed: Apr. 26, 2006

(86) PCT No.: PCT/JP2006/308736
§ 371 (c)(1), (2), (4) Date: Dec. 13, 2007

(87) PCT Pub. No.: WO2006/137217
PCT Pub. Date: Dec. 28, 2006

(65) Prior Publication Data
US 2010/0137682 A1    Jun. 3, 2010

(30) Foreign Application Priority Data

Jun. 20, 2005   (JP) .................................. 2005-179724

(51) Int. Cl.
*A61B 1/06* (2006.01)
*A61B 1/04* (2006.01)
(52) U.S. Cl. .......................... 600/168; 600/179; 600/129
(58) Field of Classification Search .................. 600/168, 600/188, 178, 173, 478, 175, 306, 158, 181, 600/179
See application file for complete search history.

(56) References Cited

U.S. PATENT DOCUMENTS

| | | | | |
|---|---|---|---|---|
| 4,500,181 A | * | 2/1985 | Takahashi | 359/503 |
| 4,671,630 A | * | 6/1987 | Takahashi | 359/503 |
| 6,447,447 B1 | * | 9/2002 | Mitsumori | 600/167 |
| 7,695,431 B2 | * | 4/2010 | Okada | 600/176 |
| 2003/0120129 A1 | | 6/2003 | Nakamura | |
| 2003/0163029 A1 | * | 8/2003 | Sonnenschein et al. | 600/160 |
| 2004/0097791 A1 | * | 5/2004 | Tokuda et al. | 600/173 |
| 2004/0122290 A1 | * | 6/2004 | Irion et al. | 600/171 |

(Continued)

FOREIGN PATENT DOCUMENTS

CN    1626027 A    6/2005

(Continued)

OTHER PUBLICATIONS

Extended Supplementary European Search Report dated Feb. 19, 2010.

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

There is provided an endoscope capable of observing cells at a desired position existing in the depth direction with a simple structure as compared to the conventional configuration. The endoscope includes an insert unit to be inserted into a biological body, a low-scaling observation system for observing an observation position in a biological body with a low scaling, and a high-scaling observation system for observing a target position of the aforementioned observation position as a local position with a high scaling. The high-scaling observation system includes a plurality of illumination units for applying illumination light for high-scaling observation of the target position. The illumination units are arranged at predetermined positions of the end face of the insert unit.

6 Claims, 2 Drawing Sheets

U.S. PATENT DOCUMENTS

| | | |
|---|---|---|
| 2004/0156124 A1 | 8/2004 | Okada |
| 2004/0158129 A1* | 8/2004 | Okada et al. ............... 600/168 |
| 2004/0210113 A1* | 10/2004 | Hasegawa .................. 600/181 |
| 2004/0212808 A1* | 10/2004 | Okawa et al. ............... 356/479 |
| 2005/0054937 A1 | 3/2005 | Takaoka et al. |
| 2005/0124858 A1* | 6/2005 | Matsuzawa et al. .......... 600/176 |
| 2005/0211872 A1* | 9/2005 | Kawano et al. ............ 250/201.3 |
| 2007/0260113 A1* | 11/2007 | Otawara ..................... 600/104 |
| 2007/0273877 A1* | 11/2007 | Kawano et al. ............. 356/318 |
| 2008/0058629 A1* | 3/2008 | Seibel et al. ................ 600/368 |
| 2008/0177144 A1* | 7/2008 | Otawara ..................... 600/157 |
| 2009/0082626 A1* | 3/2009 | Ichimura et al. ............. 600/109 |
| 2009/0093681 A1* | 4/2009 | Ichimura ..................... 600/178 |
| 2009/0253966 A1* | 10/2009 | Ichimura ..................... 600/175 |

FOREIGN PATENT DOCUMENTS

| | | |
|---|---|---|
| EP | 0 228 493 A1 | 7/1987 |
| JP | 06-154155 | 6/1994 |
| JP | 2004-159924 | 6/2004 |
| JP | 2004-166913 | 6/2004 |
| JP | 2005-013484 | 1/2005 |
| JP | 2005-040175 | 2/2005 |

* cited by examiner

ENDOSCOPE

TECHNICAL FIELD

The present invention relates to an endoscope, and more particularly to an endoscope capable of performing histological observation in a living body.

BACKGROUND ART

In recent years, histological observation of a cell in a living body has been brought to attention for its importance in early detection and early diagnostics of cancer.

As an apparatuses enabling histological observation of a cell in a living body, there is proposed an apparatus such as an endoscope or the like capable of performing observation of a desired region existing in a depth direction by using a confocal image, for example.

In addition, as an apparatus enabling histological observation of a cell in a living body, for example, there is proposed an apparatus such as an endoscope or the like capable of performing magnifying observation at a magnification 20 to 100 times higher than an ordinary microscope, in addition to observation at a normal magnification.

An endoscope proposed in Japanese Unexamined Patent Application Publication No. 2004-159924 includes a microscopic observation optical system for performing the magnifying observation and a focus adjustment mechanism for moving a subject side focus position of the microscopic observation optical system, in a distal end of an insertion portion insertable into a subject's body. Therefore, the endoscope is capable of generating a confocal image for observing a cell at a desired region existing in a depth direction with the above-described configuration.

On the other hand, an optical observation probe and an endoscope observation apparatus proposed in Japanese Unexamined Patent Application Publication No. 2004-166913 include normal magnification image pickup means and high magnification image pickup means. Therefore, the optical observation probe and the endoscope observation apparatus are capable of performing normal magnification observation and histological observation, i.e., magnifying observation with respect to a cell at a desired region existing on a surface layer of a living tissue with the above-described configuration.

However, the endoscope proposed in Japanese Unexamined Patent Application Publication No. 2004-159924 has a problem of high cost at the time of manufacturing, because of the complicated configuration for generating a confocal image.

In addition, the optical observation probe and the endoscope observation apparatus proposed in Japanese Unexamined Patent Application Publication No. 2004-166913 have a problem that an observable area is limited to a cell on the surface layer of the living tissue, because of structural difficulty in performing observation of a cell at a desired region existing in a depth direction in the histological observation.

The present invention has been made in view of the above-described points and an object of the present invention is to provide an endoscope enabling observation of a cell at a desired region existing in a depth direction with a configuration simpler than a conventional one.

DISCLOSURE OF INVENTION

Means for Solving the Problem

An endoscope of the first aspect of the present invention includes: an insertion portion to be inserted into a living body; a low magnification observation system for performing low magnification observation at a region to be observed in the living body, the low magnification observation system being provided to the insertion portion; a high magnification observation system for performing high magnification observation at a region of interest which is a local region of the region to be observed, the high magnification observation system being provided to the insertion portion; wherein the high magnification observation system includes a plurality of illumination portions for respectively illuminating illumination lights for high magnification observation with respect to the region of interest, and the plurality of illumination portions are respectively arranged at predetermined positions on a distal end surface of the insertion portion.

The endoscope of a second aspect of the present invention is the endoscope of the first aspect, wherein the high magnification observation system includes an illumination optical system for high magnification observation and an image pickup optical system for high magnification observation, and the predetermined positions have different distances from an optical axis of the image pickup optical system for high magnification observation.

The endoscope of a third aspect of the present invention is the endoscope of the second aspect, wherein the illumination lights for high magnification observation irradiated from the plurality of illumination portions respectively have different wavelength bands.

The endoscope of a fourth aspect of the present invention is the endoscope of the second aspect, wherein the illumination lights for high magnification observation irradiated from the plurality of illumination portions respectively have approximately same wavelength bands.

The endoscope of a fifth aspect of the present invention is the endoscope of the second aspect, wherein the illumination portions are configured of LEDs.

The endoscope of a sixth aspect of the present invention is the endoscope of the third aspect, wherein the illumination portions are configured of LEDs.

The endoscope of the seventh aspect of the present invention is the endoscope of the fourth aspect, wherein the illumination portions are configured of LEDs.

The endoscope of the eighth aspect of the present invention is the endoscope of the first aspect, wherein the high magnification observation system includes an illumination optical system for high magnification observation and an image pickup optical system for high magnification observation, and the predetermined positions have the approximately same distances from an optical axis of the image pickup optical system for high magnification observation.

The endoscope of the ninth aspect of the present invention is the endoscope of the eighth aspect, wherein the illumination lights for high magnification observation irradiated from the plurality of illumination portions respectively have different wavelength bands.

The endoscope of the tenth aspect of the present invention is the endoscope of the eighth aspect, wherein the illumination portions are configured of LEDs.

The endoscope of the eleventh aspect of the present invention is the endoscope of the ninth aspect, wherein the illumination portions are configured of LEDs.

The endoscope of the twelfth aspect of the present invention is the endoscope of the first aspect, wherein the illumination lights for high magnification observation irradiated from the plurality of illumination portions respectively have different wavelength bands.

The endoscope of the thirteenth aspect of the present invention is the endoscope of the twelfth aspect, wherein the illumination portions are configured of LEDs.

The endoscope of the fourteenth aspect of the present invention is the endoscope of the first aspect, wherein the illumination lights for high magnification observation irradiated from the plurality of illumination portions respectively have approximately same wavelength bands.

The endoscope of the fifteenth aspect of the present invention is the endoscope of the fourteenth aspect, wherein the illumination portions are configured of LEDs.

The endoscope of the sixteenth aspect of the present invention is the endoscope of the first aspect, wherein the illumination portions are configured of LEDs.

BEST MODE FOR CARRYING OUT THE INVENTION

Figure 1:
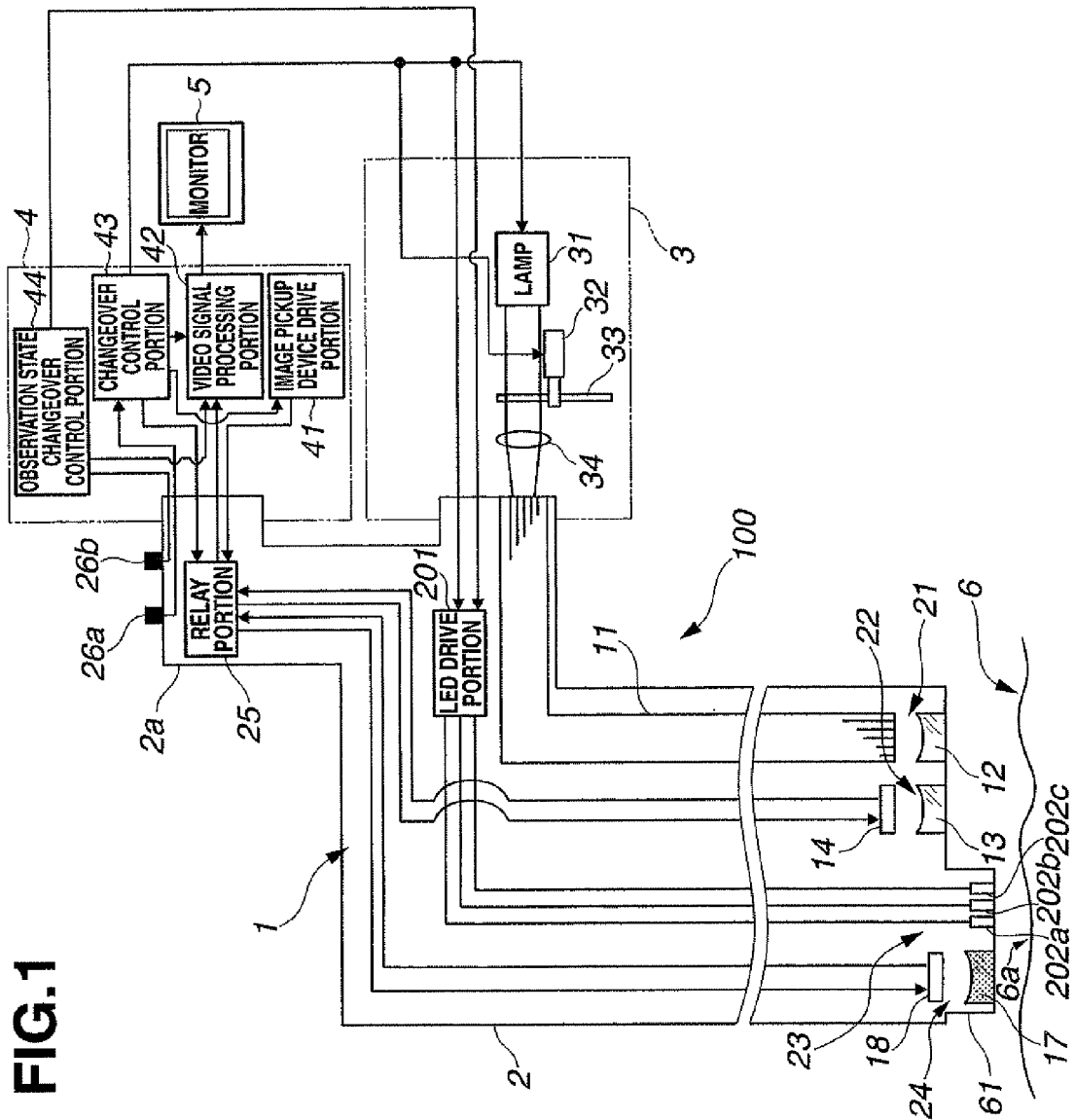
FIG. 1 is a diagram showing an exemplary configuration of an endoscope apparatus using an endoscope according to a present embodiment.
Figure 2:
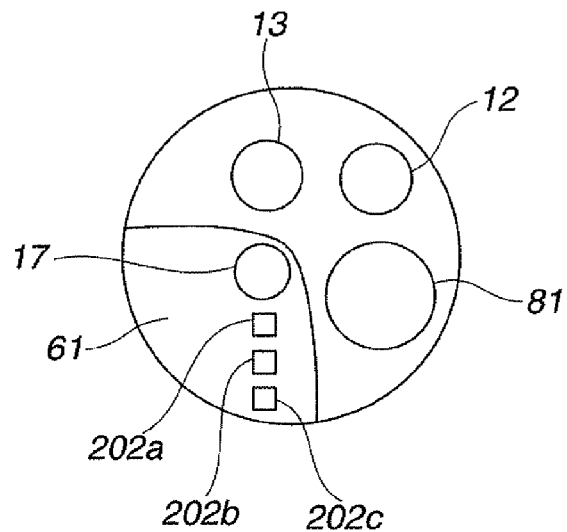
FIG. 2 is a diagram showing an exemplary configuration of a distal end surface of the endoscope according to the present embodiment.
Figure 3:
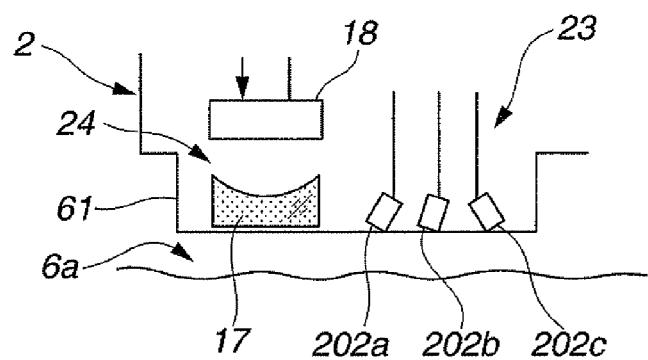
FIG. 3 is a diagram showing an exemplary configuration different from that in FIG. 1, of a projection portion of the endoscope according to the present embodiment.
Figure 4:
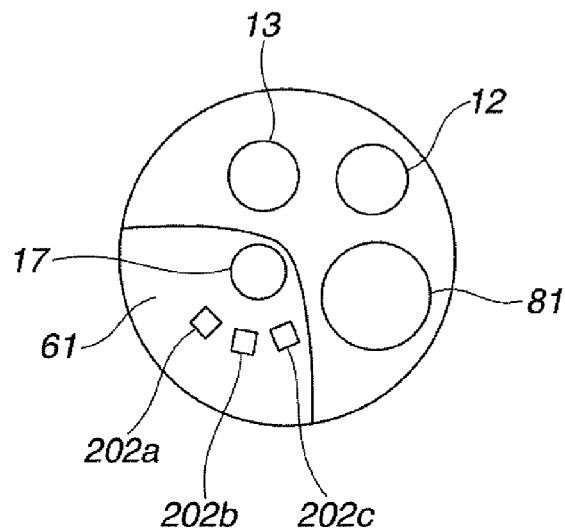
FIG. 4 is a diagram showing an exemplary configuration different from that in FIG. 2, of a distal end surface of the endoscope according to the present embodiment.

Hereinafter, an embodiment of the present invention will be described with reference to the drawings. FIG. 1 is a diagram showing an exemplary configuration of an endoscope apparatus using an endoscope according to the present embodiment. FIG. 2 is a diagram showing an exemplary configuration of a distal end surface of the endoscope according to the present embodiment. FIG. 3 is a diagram showing an exemplary configuration different from that in FIG. 1, of a projection portion of the endoscope according to the present embodiment. FIG. 4 is a diagram showing an exemplary configuration different from that in FIG. 2, of a distal end surface of the endoscope according to the present embodiment.

As shown in FIG. 1, an endoscope apparatus 100 includes as a main part: an endoscope 1 a part of which is inserted in a living body as a subject; a light source device 3 for supplying to the endoscope 1 illumination light for normal observation used in normal observation as an observation at a low magnification; a processor 4 for performing signal processing on an image pickup signal outputted from the endoscope 1; and a monitor 5 for displaying an endoscope picture and the like based on a video signal outputted from the processor 4. In addition, the endoscope 1 includes a flexible insertion portion 2 to be inserted in a living body and an operation portion 2a provided on a rear end side of the insertion portion 2.

The insertion portion 2 includes inside thereof an illumination optical system for normal observation 21 for transmitting illumination light for normal observation emitted from the light source device 3 and irradiating the illumination light to a front of a distal end side of the insertion portion 2, and an image pickup optical system for normal observation 22 for picking up an image of a region to be observed 6 as a living tissue and the like illuminated by the illumination optical system for normal observation 21.

Furthermore, the insertion portion 2 is provided with an illumination optical system for magnifying observation 23 for irradiating illumination light for magnifying observation as illumination light for high magnification observation to the front of the distal end side of the insertion portion 2, and an image pickup optical system for magnifying observation 24 for picking up an image of a region of interest 6a illuminated by the illumination optical system for magnifying observation 23. Note that the region of interest 6a is, within the region to be observed 6, a local region in the living tissue and the like on which magnifying observation as high magnification observation is performed.

The illumination optical system for normal observation 21 as an illumination optical system for low magnification observation includes a light guide 11 for transmitting illumination light for normal observation, and an illumination lens 12 for irradiating the illumination light for normal observation transmitted by the light guide 11 to the front of the distal end side of the insertion portion 2 and illuminating the region to be observed 6.

The image pickup optical system for normal observation 22 as the image pickup optical system for low magnification observation includes an objective lens 13 for forming the image of the region to be observed 6 illuminated by the illumination light for normal observation, and an image pickup device 14 such as a CCD or the like, for example, which is provided at an image-forming position of the objective lens 13, for picking up the image of the region to be observed 6 and outputting the picked up image as an image pickup signal.

The low magnification observation system according to the present embodiment includes the above-described illumination optical system for normal observation 21 and the image pickup optical system for normal observation 22.

On the other hand, the illumination optical system for magnifying observation 23 as an illumination optical system for high magnification observation includes, for example, a plurality of LEDs for irradiating the illumination light for magnifying observation to the front of the distal end side of the insertion portion 2. Note that, though description will be made below assuming that the illumination optical system for magnifying observation 23 includes three LEDs, that is, an LED 202a, an LED 202b, and an LED 202c as illumination portions, the configuration is not limited thereto. The illumination optical system for magnifying observation 23 may include two LEDs or more than four LEDs, for example.

The LEDs 202a, 202b, and 202c are respectively driven and emit light based on LED drive control signals to be outputted from an LED drive portion 201 to be described later, and irradiate to the front of the distal end side of the insertion portion 2 illumination lights having, for example approximately the same predetermined wavelength band, as illumination lights for magnifying observation. Note that the illumination lights for magnifying observation irradiated by the LEDs 202a, 202b, and 202c may have, for example, a wavelength band corresponding to optical characteristics of a dye to be sprayed to the region of interest 6a and hemoglobin in the blood as the predetermined wavelength band.

In addition, the image pickup optical system for magnifying observation 24 as an image pickup optical system for high magnification observation includes: an objective lens 17 as an objective optical system for forming the image of the region of interest 6a illuminated by the illumination light for magnifying observation; and an image pickup device 18 such as CCD or the like, for example, which is provided at an image forming position of the objective lens 17, for picking up the image of the region of interest 6a and outputting the picked up image as an image pickup signal.

The high magnification observation system in the present embodiment includes the above-described illumination optical system for magnifying observation 23 and the image pickup optical system for magnifying observation 24.

The light source device 3 includes a lamp 31 configured of a xenon lamp, for example, as a light source for normal observation which emits white light, a motor 32, an RGB filter portion 33 driven and rotated by the motor 32, and a lens 34 for condensing on an incident end of the light guide 11 the illumination light for normal observation which is the illumination light radiated from the lamp 31 to be emitted via the RGB filter portion 33.

The RGB filter portion 33 has a configuration in which filters which transmit lights of R, G, and B wavelength bands, respectively, are sequentially and continuously interposed on an optical axis of the lamp 31 when rotated by the motor 32.

Note that it is assumed that the illumination optical system for normal observation 21, the image pickup optical system for normal observation 22, the lamp 31, the RGB filter portion 33, and the lens 34 are optical systems respectively having configurations optimized for the normal observation as the low magnification observation. Note that, the filters not shown for transmitting lights of R, G, and B wavelength bands, which are provided to the RGB filter portion 33, respectively have transmissivities optimized for normal observation as the low magnification observation.

In addition, it is assumed that the illumination optical system for magnifying observation 23 and the image pickup optical system for magnifying observation 24 are optical systems respectively having configurations optimized for magnifying observation.

The operation portion 2a of the endoscope 1 includes a relay portion 25 and the LED drive portion 201 inside thereof and also an observation changeover switch 26a and an observation state changeover switch 26b on an exterior surface thereof.

The observation changeover switch 26a is configured as a switch for changing over between normal observation and magnifying observation, and outputs observation changeover instruction signal to the processor 4 when operated by an operator or the like. The observation changeover instruction signal outputted from the observation changeover switch 26a is inputted to the processor 4. The processor 4 outputs control signals to the relay portion 25, the LED drive portion 201, and the light source device 3 based on the observation changeover instruction signal outputted from the observation changeover switch 26a.

The relay portion 25 configured of a relay circuit and the like changes over drive states and image pickup states of the image pickup devices 14 and 18 based on the control signal outputted from the processor 4.

In addition, the LED drive portion 201 performs control to turn on or off any one or more of the LEDs 202a, 202b, and 202c, based on the control signal outputted from the processor 4.

In addition, the light source device 3 changes the irradiation state of the illumination light for normal observation by performing controls on the lamp 31 and the motor 32 based on the control signal outputted from the processor 4.

The observation state changeover switch 26b is configured as a switch capable of selecting one or more LEDs to be turned on out of the plurality of LEDs included in the illumination optical system for magnifying observation 23, in a case where magnifying observation is performed, and also capable of selecting a signal processing method to be performed in the processor 4 in a case where the region of interest 6a is illuminated by the illumination light for magnifying observation irradiated from the selected one or more of the LEDs. Then, the observation state changeover switch 26b outputs an observation state changeover instruction signal to the processor 4, when operated by an operator or the like. The observation state changeover instruction signal outputted from the observation state changeover switch 26b is inputted to the processor 4. The processor 4 outputs the control signal to the LED drive portion 201 based on the observation state changeover instruction signal outputted from the observation state changeover switch 26b, and outputs the image pickup signal processed by the signal processing method selected by the operation of the observation state changeover switch 26b to the monitor 5 as a video signal.

The LED drive portion 201 performs control to turn on or off the one or more LEDs selected among the LEDs 202a, 202b, and 202c by the operation of the observation state changeover switch 26b, based on the control signal outputted from the processor 4.

The processor 4 includes an image pickup device drive portion 41 for generating a CCD drive signal to drive either one of the image pickup device 14 or the image pickup device 18, a video signal processing portion 42, a changeover control portion 43, and an observation state changeover control portion 44.

The video signal processing portion 42 performs signal processing on an image pickup signal outputted from the image pickup device 14 or the image pickup device 18 via the relay portion 25 and also performs signal processing to cause the monitor 5 to display an endoscope picture or a magnifying observation picture.

In addition, in a case where magnifying observation is performed, that is, when detecting that an image pickup signal is outputted from the image pickup device 18, the video signal processing portion 42 performs signal processing such as dimming on the image pickup signal using the signal processing method selected by the operation of the observation state changeover switch 26b based on the control signal outputted from the observation state changeover control portion 44. Then, the video signal processing portion 42 outputs to the monitor 5 the image pickup signal subjected to the signal processing as a video signal.

The changeover control portion 43, in response to the observation changeover instruction signal outputted from the observation changeover switch 26a, outputs to the relay portion 25, the lamp 31, the motor 32, the image pickup device drive portion 41, and the video signal processing portion 42, control signals for changing over between normal observation and magnifying observation based on the observation changeover instruction signal outputted from the observation changeover switch 26a.

For example, when a first instruction signal is outputted from the changeover switch 26a by operation by an operator or the like, the changeover control portion 43 outputs the control signal for performing such controls as to cause the relay portion 25 to terminate the connection between the image pickup device 18 and the processor 4, to output the drive signal from the image pickup device drive portion 41 to the image pickup device 14, and moreover, to output the image pickup signal from the image pickup device 14 to the video signal processing portion 42.

Furthermore, when the first instruction signal is outputted from the changeover switch 26a, the changeover control portion 43 outputs control signals to cause the image pickup device drive portion 41 and the video signal processing portion 42 to perform signal processing for normal observation as processing with respect to the image pickup device 14. Accordingly, the monitor 5 displays, as an endoscope picture, the image of the region to be observed 6 as the image of normal observation, based on the video signal outputted from the video signal processing portion 42.

Furthermore, when the first instruction signal is outputted from the changeover switch 26*a*, the changeover control portion 43 outputs a control signal to light the lamp 31 and start rotational driving of the motor 32.

In addition, when a second instruction signal is outputted from the changeover switch 26*a* by an operation by an operator or the like, for example, the changeover control portion 43 outputs a control signal for performing such controls as to cause the relay portion 25 to terminate the connection between the image pickup device 14 and the processor 4, to output the drive signal from the image pickup device drive portion 41 to the image pickup device 18, and moreover, to output the image pickup signal from the image pickup device 18 to the video signal processing portion 42.

Then, when the second instruction signal is outputted from the changeover switch 26*a*, the changeover control portion 43 outputs control signals to cause the image pickup device drive portion 41 and the video signal processing portion 42 to perform signal processing for magnifying observation as processing with respect to the image pickup device 18. Note that, in the present embodiment, it is assumed that the video signal processing portion 42 detects that an image pickup signal is being outputted from the image pickup device 18 by detecting that the control signal based on the second instruction signal has been outputted from the changeover control portion 43. Furthermore, in the present embodiment, it is assumed that the video signal processing portion 42 performs, based on the detection result, signal processing, as the signal processing for the magnifying observation, using the signal processing method selected by the operation of the observation state changeover switch 26*b* based on the control signal outputted from the observation state changeover control portion 44 as described above. Accordingly, the monitor 5 displays, as a magnifying observation picture, the image of the region of interest 6*a* as an image of magnifying observation based on the video signal outputted from the video signal processing portion 42.

Moreover, when the second instruction signal is outputted from the changeover switch 26*a*, the changeover control portion 43 outputs a control signal to put off the lamp 31 and stop the rotational driving of the motor 32.

Based on the observation state changeover instruction signal outputted from the observation state changeover switch 26*b*, the observation state changeover control portion 44 outputs a control signal for performing such a control as to cause the video signal processing portion 42 to perform signal processing using a signal processing method selected by an operation of the observation state changeover switch 26*b*. In addition, based on the observation state changeover instruction signal outputted from the observation state changeover switch 26*b*, the observation state changeover control portion 44 outputs a control signal for performing such a control as to cause the LED drive portion 201 to turn on or off the one or more LEDs selected by the operation of the observation state changeover switch 26*b*.

Note that a projection portion 61 projected from the distal end surface of the insertion portion 2 of the endoscope 1 is provided with the LEDs 202*a*, 202*b*, and 202*c* which are the plurality of LEDs included in the illumination optical system for magnifying observation 23 and the objective lens 17 of the image pickup optical system for magnifying observation 24.

Furthermore, the portions included in the insertion portion 2 are arranged on the distal end surfaces of the insertion portion 2 and the projection portion 61 at positions shown in FIG. 2, respectively, for example.

The LEDs 202*a*, 202*b*, and 202*c* are arranged on the distal end surface of the projection portion 61 at positions whose distances from the optical axis of the objective lens 17 are different, respectively. For example, in the present embodiment, as shown in FIG. 2, the LED 202*a* is arranged at the position whose distance from the optical axis of the objective lens 17 is the closest, the LED 202*c* being arranged at the position whose distance from the optical axis of the objective lens 17 is the furthest, the LED 202*b* being arranged at the position whose distance from the optical axis of the objective lens 17 is further than the position of the LED 202*a* and closer than that of the LED 202*c*.

A treatment instrument projection port 81 arranged on the distal end surface of the insertion portion 2 is in communication with a treatment instrument insertion channel, not shown, provided so as to pass through the insertion portion 2.

Next, description will be made on an action of the endoscope apparatus 100.

First, an operator or the like connects each of the portions of the endoscope apparatus 100 and turns on a power source of each of the portions. After that, the operator or the like operates the changeover switch 26*a* to cause the first instruction signal to be outputted from the changeover switch 26*a*, to bring each of the portions of the endoscope apparatus 100 into a state for normal observation. Then, the operator or the like inserts the insertion portion 2 of the endoscope 1 into a living body, while looking at an endoscope picture displayed on the monitor 5.

Furthermore, when the insertion portion 2 reaches the desired region to be observed 6 including the region of interest 6*a*, the operator or the like performs operation to bring the distal end surface of the projection portion 61 of the insertion portion 2 into contact with the region of interest 6*a*. After that, the operator or the like operates the changeover switch 26*a* to cause the second instruction signal to be outputted from the changeover switch 26*a*, to bring each of the portions of the endoscope apparatus 100 into a state for magnifying observation.

Then, when each of the portions of the endoscope apparatus 100 is in the state for magnifying observation, the operator or the like operates the observation state changeover switch 26*b* to select an LED to be turned on among the LEDs 202*a*, 202*b*, and 202*c*, and also selects a signal processing method performed in the processor 4 when the selected LED is being turned on.

For example, by the operation of the observation state changeover switch 26*b* by the operator or the like is outputted the observation state changeover instruction signal for turning on the LED 202*a* and making the processor 4 execute the signal processing method in the case where the LED 202*a* is turned on. Based on the observation state changeover instruction signal outputted from the observation state changeover switch 26*b*, the processor 4 controls the LED drive portion 201 to turn on the LED 202*a* and performs signal processing using the signal processing method selected by the operation of the observation changeover switch 26*b*.

The objective lens 17 forms an image by reflected light reflected near a surface layer of the region of interest 6*a* out of the illumination light for magnifying observation irradiated from the LED 202*a*. As a result, the image pickup device 18 picks up the image near the surface layer of the region of interest 6a in a field of view area of the objective lens 17, to output the image near the surface layer as an image pickup signal.

The image pickup signal outputted from the image pickup device 18 is inputted to the video signal processing portion 42 via the relay portion 25. The video signal processing portion 42 performs signal processing such as dimming on the image pickup signal using the signal processing method selected by the operation of the observation state changeover switch 26b, and outputs the image pickup signal subjected to the processing to the monitor 5 as a video signal. As a result, the image near the surface layer of the region of interest 6a is displayed as a magnifying observation picture on the monitor 5.

In addition, for example, by the operation of the observation state changeover switch 26b by the operator or the like is outputted the observation state changeover instruction signal for turning on the LED 202b and making the processor 4 execute the signal processing method in the case where the LED 202b is turned on. Based on the observation state changeover instruction signal outputted from the observation state changeover switch 26b, the processor 4 controls the LED drive portion 201 to turn on the LED 202b and performs a signal processing using the signal processing method selected by the operation of the observation state changeover switch 26b.

The objective lens 17 forms an image by reflected light reflected on a first layer of the region of interest 6a separated by a first distance from the surface layer of the region of interest 6a in a depth direction out of the illumination light for magnifying observation irradiated from the LED 202b. As a result, the image pickup device 18 picks up the image of the first layer of the region of interest 6a in a field of view area of the objective lens 17, to output the image of the first layer as an image pickup signal. Note that the first distance is supposed to be a predetermined distance corresponding to the distance between the optical axis of the objective lens 17 and the arranging position of the LED 202b.

The image pickup signal outputted from the image pickup device 18 is inputted to the video signal processing portion 42 via the relay portion 25. The video signal processing portion 42 performs signal processing such as dimming on the image pickup signal using the signal processing method selected by the operation of the observation state changeover switch 26b, and outputs the image pickup signal subjected to the processing to the monitor 5 as a video signal. As a result, the image of the first layer of the region of interest 6a is displayed on the monitor 5 as a magnifying observation picture, the first layer being separated by the first distance from the surface layer of the region of interest 6a in the depth direction.

Moreover, for example, by the operation of the observation state changeover switch 26b by the operator or the like is outputted the observation state changeover instruction signal for turning on the LED 202c and making the processor 4 execute the signal processing method in the case where the LED 202c is turned on. Based on the observation state changeover instruction signal outputted from the observation state changeover switch 26b, the processor 4 controls the LED drive portion 201 to turn on the LED 202c and performs a signal processing using the signal processing method selected by the operation of the observation state changeover switch 26b.

The objective lens 17 forms an image by reflected light reflected on a second layer of the region of interest 6a existing at a position deeper than the first layer and separated by a second distance from the surface layer of the region of interest 6a in the depth direction, out of the illumination light for magnifying observation irradiated from the LED 202c. As a result, the image pickup device 18 picks up the image of the second layer of the region of interest 6a in a field of view area of the objective lens 17, to output the image of the second layer as an image pickup signal. Note that the second distance is supposed to be a predetermined distance corresponding to the distance between the optical axis of the objective lens 17 and the arranging position of the LED 202c.

The image pickup signal outputted from the image pickup device 18 is inputted to the video signal processing portion 42 via the relay portion 25. The video signal processing portion 42 performs signal processing such as dimming on the image pickup signal using the signal processing method selected by the operation of the observation state changeover switch 26b, and outputs the image pickup signal subjected to the processing to the monitor 5 as a video signal. As a result, the image of the second layer of the region of interest 6a is displayed on the monitor 5 as a magnifying observation picture, the second layer being separated by the second distance from the surface layer of the region of interest 6a in the depth direction.

Note that the LEDs 202a, 202b, and 202c may be configured such that a plurality of the LEDs are simultaneously turned on. In that case, out of the image near the surface layer of the region of interest 6a, the image of the first layer of the region of interest 6a, and the image of the second layer of the region of interest 6a, a plurality of the images picked up corresponding to the plurality of light emitting LEDs are displayed in a superimposed manner.

In addition, the LEDs 202a, 202b, and 202c are not limited to ones which irradiate illumination lights for magnifying observation having approximately the same wavelength bands. For example, the LEDs 202a, 202b, and 202c may be configured to emit illumination lights for magnifying observation each having a different wavelength band such that: the LED 202a irradiates illumination light for magnifying observation having the shortest wavelength band; the LED 202c irradiates illumination light for magnifying observation having the longest wavelength band; and the LED 202b irradiates illumination light for magnifying observation having a wavelength band different from those of the LED 202a and the LED 202c. With the LEDs 202a, 202b, and 202c configured as described above, when illumination light for magnifying observation is irradiated from the LED 202c, for example, the image pickup device 18 can pick up an image of a third layer of the region of interest 6a, the third layer existing at a position deeper than the second layer and being separated by a third distance from the surface layer of the region of interest 6a in the depth direction.

Furthermore, the LEDs 202a, 202b, and 202c are not limited to ones configured to irradiate illumination lights for magnifying observation to the front of the distal end side of the insertion portion 2, that is, to approximately the same irradiation directions. For example, as shown in FIG. 3, the LEDs 202a, 202b, and 202c may be configured to irradiate the illumination lights for magnifying observation in different irradiation directions, respectively, in front of the distal end side of the insertion portion 2, with the LEDs arranged so as to have different angles with respect to the front direction of the distal end side of the insertion portion 2.

Note that, as a configuration having generally the same action as that described above, for example, the LEDs 202a, 202b, and 202c may be arranged on the distal end surface of the projection portion 61 at the positions as shown in FIG. 4, respectively.

Specifically, the LEDs 202a, 202b, and 202c are arranged on the distal end surface of the projection portion 61 at positions whose distances from the optical axis of the objective lens 17 are approximately the same, respectively, as shown in FIG. 4. Furthermore, in addition to the arranging state as described above, the LEDs 202a, 202b, and 202c are configured to irradiate illumination lights for magnifying observation respectively having different wavelength bands such that: the LED 202a irradiates the illumination light for magnifying observation having the shortest wavelength band; and the LED 202c irradiates the illumination light for magnifying observation having the longest wavelength band.

With the LEDs 202a, 202b, and 202c arranged and configured as described above, the image pickup device 18, for example, can pick up the image near the surface layer of the region of interest 6a when the illumination light for magnifying observation is irradiated from the LED 202a, the image of the first layer of the region of interest 6a when the illumination light for magnifying observation is irradiated from the LED 202b, and the image of the second layer of the region of interest 6a when the illumination light for magnifying observation is irradiated from the LED 202c.

Note that, though the endoscope apparatus 100 of the present embodiment includes the endoscope 1 integrally provided with the illumination optical system and image pickup optical system for normal observation and the illumination optical system and image pickup optical system for magnifying observation, there is no limitation placed thereon. As long as being configured to have the action generally the same as that described above, the endoscope apparatus 100 of the present embodiment may include, as a main part, an endoscope having an illumination optical system and image pickup optical system for normal observation, and a probe insertable through a treatment instrument insertion channel of the endoscope which includes an illumination optical system and an image pickup optical system for magnifying observation provided at a distal end portion thereof, for example.

As described above, the endoscope apparatus 100 of the present embodiment enables the observation of a cell at a desired region existing in a depth direction with easier configuration compared with the conventional one, without having a complicated configuration such as one for moving a subject side focus position of the observation optical system, for example. As a result, the endoscope apparatus 100 of the present embodiment can improve diagnostic performance when an operator or the like performs histological observation on a cell in a living body.

Note that the present invention is note limited to the embodiments described above, and it is apparent that various changes and modifications are possible without departing from the spirit and scope of the invention.

This application claims the priority of Japanese Patent Application No. 2005-179724 filed on Jun. 20, 2005, the content of which is incorporated in the specification, claims and drawings.

The invention claimed is:

1. An endoscope, comprising:
an insertion portion to be inserted into a living body;
a low magnification observation system for performing low magnification observation at a region to be observed in the living body, the low magnification observation system being provided to the insertion portion; and
a high magnification observation system for performing high magnification observation at a region of interest which is a local region of the region to be observed, the high magnification observation system being provided to a projection portion projected from a distal end surface of the insertion portion;
wherein the high magnification observation system includes an image pickup optical system for high magnification observation and a plurality of illumination portions included in an illumination optical system for high magnification observation, for respectively irradiating illumination lights for high magnification observation with respect to the region of interest;
wherein the plurality of illumination portions are respectively arranged at positions on a distal end surface of the projection portion, the positions being at mutually different distances from an optical axis of the image pickup optical system for high magnification observation, the positions enabling the illumination lights for high magnification observation to be irradiated to layers at mutually different depths at the region of interest.

2. The endoscope according to claim 1, wherein the plurality of illumination portions are configured to respectively irradiate lights of mutually different wavelength bands as illumination lights for high magnification observation.

3. The endoscope according to claim 1, wherein the plurality of illumination portions are configured to respectively irradiate lights of mutually approximately the same wavelength bands as illumination lights for high magnification observation.

4. The endoscope according to claim 1, wherein the illumination portions are configured of LEDs.

5. The endoscope according to claim 2, wherein the illumination portions are configured of LEDs.

6. The endoscope according to claim 3, wherein the illumination portions are configured of LEDs.

* * * * *